United States Patent [19]

Whiting

[11] Patent Number: Plant 6,841

[45] Date of Patent: Jun. 6, 1989

[54] CYNODON DACTYLON GRASS PLANT CT-2

[76] Inventor: Hubert F. Whiting, 3771 Mattei Rd., Santa Ynez, Calif. 93460

[21] Appl. No.: 129,783

[22] Filed: Nov. 30, 1987

[51] Int. Cl.[4] ..... A01H 5/00

[52] U.S. Cl. ..... Plt./88

[58] Field of Search ..... Plt./88

*Primary Examiner*—Robert E. Bagwill

[57] ABSTRACT

I disclose that my herein invention of a new and distinct variety of Cynodon Dactylon grass plant, that was discovered by me through a series of cross-pollination of selected varieties of Cynodon Dactylon grass plants, then through asexually repropagation selected the new and distinct variety of Cynodon Dactylon grass plant CT-2. This new variety produces an excellent turfgrass surface of a very dark green color, with less thatch build-up. The entire plant is pubescent and the electrophoresis isoenzyme banding patterns show distinct uniqueness of this new variety CT-2.

2 Drawing Sheets

The present invention and discovery relates to a new and distinct variety of Cynodon Dactylon grass plant, which was developed by me through a series of cross-pollination of collected varieties of Cynodon Dactylon grass plants, selecting mostly for improved color, winter color retention and less thatch build-up. This cross-pollination was done by me at Fallbrook, Calif., U.S.A. about 34 degrees north latitude. I harvested seeds from this series of cross-pollination of Cynodon Dactylon grass plants and planted these seeds out in germinating trays. About six weeks after the seeds germinated, I then planted these seeds in one gallon containers, to further evaluate their color and growth characteristics. I selected several geneotypes from the one gallon containers and by breaking the stolons into pieces I asexually planted them out in field trials, for further evaluation for color, winter green color retention and lack of thatch build-up. CT-2 is the final selection from my field trials. This new claimed variety of Cynodon Dactylon grass plant designated CT-2, produced an excellent turfgrass surface under field trials, when compared to the closest known variety of Cynodon Dactylon grass plant, which is identified as the claimed variety of Cynodon Dactylon grass plant, of my U.S. plant patent application Ser. No 06/825-449 filed 02/03/86 and identified as C84-135. During the continued asexual reproduction by stolon planting I have confirmed that the above described characteristics are transmitted through succeeding propagations, and have confirmed that the new claimed variety of Cynodon Dactylon grass plant has the following unique combination of characteristics. The new and distinct variety of Cynodon Dactylon grass plant is illustrated in the accompanying color photographs, with photographs of the closest known variety of Cynodon Dactylon grass plant identified as C84-135. The most noticeable variations between the new claimed variety of Cynodon Dactylon grass plant, and the closest known variety C84-135, is that the new claimed variety of Cynodon Dactylon grass plant is a very dark green color, when compared to the closest known variety which is a dark olive green color. The new claimed variety also has a less thatch build-up characteristic, with a better winter green color retention. The new claimed variety of Cynodon Dactylon grass plant is entirely pubescent, when compared to the closest known variety of Cynodon Dactylon grass plant which is glabrous, except for a few hairs tufted at the sides of the ligule and pubescent on the upper leaf surface. This new claimed variety of Cynodon Dactylon grass plant, has anthers before dehiscence, of light yellow green color, when compared to the closest known variety which has grayish red colored anthers. The new claimed variety of Cynodon Dactylon grass plant CT-2, has unique isoenzyme electrophoresis banding patterns, when compared to the closest known variety of Cynodon Dactylon grass plant C84-135.

Figure 1:
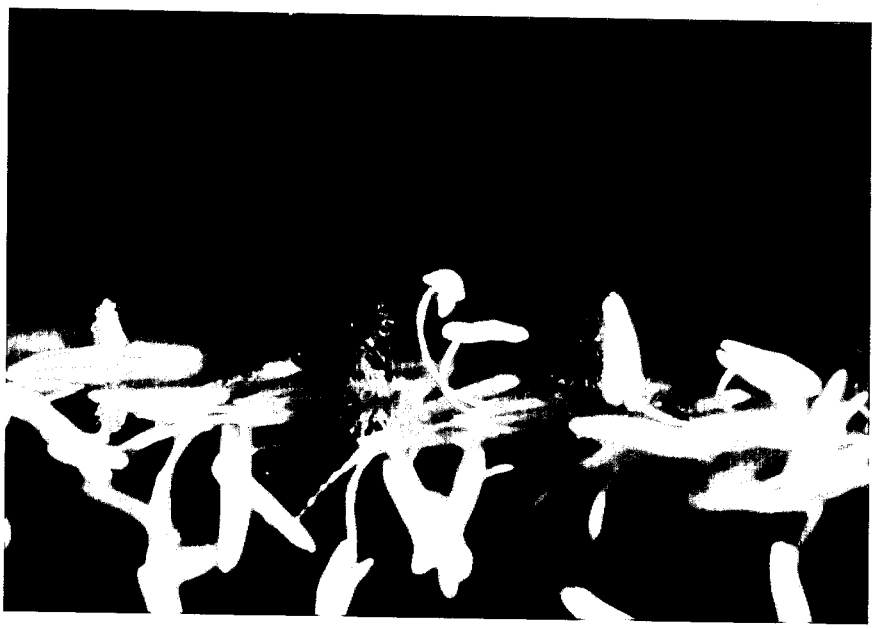
FIG. 1 is a photograph of a spike taken from the same test area, of the new and distinct variety of Cynodon Dactylon grass plant. This photograph shows the very deep purplish red colored stigmas, color number 257 V.deep Pr of the ISCC-NBS centroid color chart and the light yellow green colored anthers, color number 119 l.YG of the ISCC-NBS centroid color chart.
Figure 2:
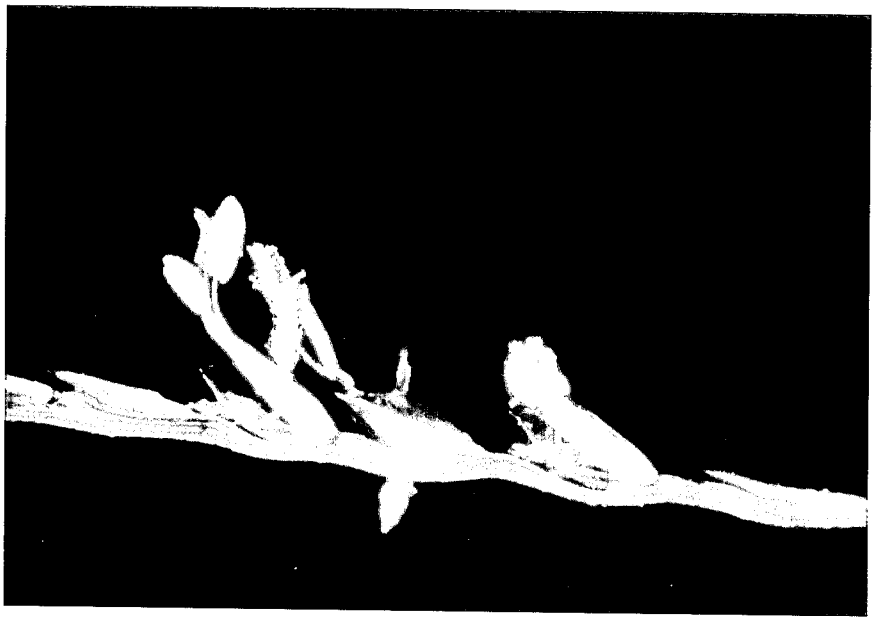
FIG. 2 is a photograph of a spike taken from the same test area, of the closest known variety of Cynodon Dactylon grass plant C184-135. This photograph shows the very dark purplish red colored stigmas, color number 260 v.dpr of the ISCC-NBS centroid color chart and the grayish red colored anthers, color number 19 gy.red of the ISCC-NBS centroid color chart.
Figure 3:
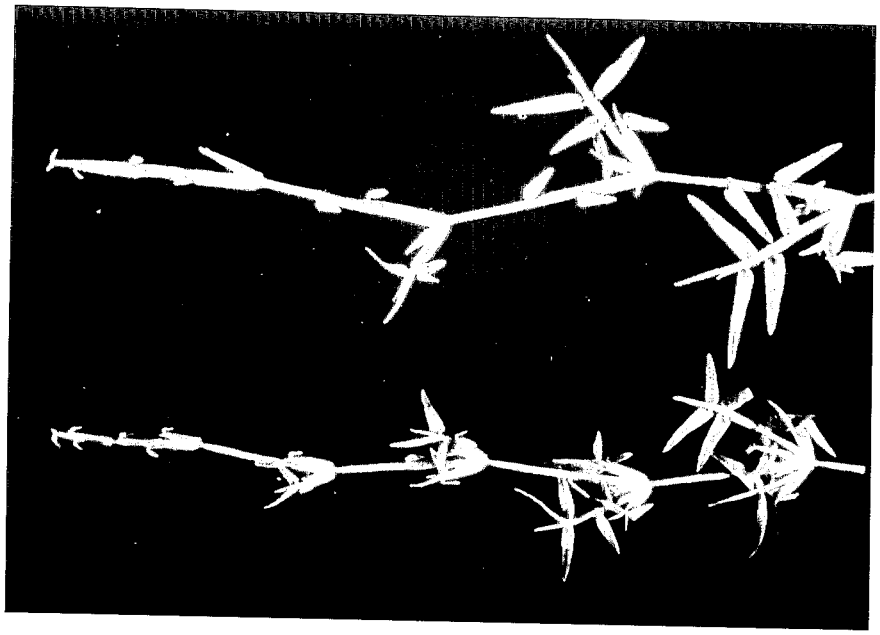

FIG. 3 is a photograph of two pieces of stolons taken from the same test area, the top stolon in the photograph is of the new claimed variety of Cynodon Dactylon grass plant CT-2, the bottom stolon in the photograph is of the closest known variety of Cynodon Dactylon grass plant C84-135. This photograph shows the internodal spaces of the new claimed variety are farther apart than the closest known variety, with the leaf length and width, greater of the new claimed variety. This photograph also shows the darker green color of the new claimed variety CT-2, when compared to the closest known variety C84-135.

Figure 4:
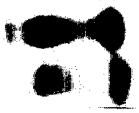

FIG. 4 this photograph shows the electrophoresis zymogram patterns of esterase (EST) isoenzyme banding pattern of the new claimed variety of Cynodon Dactylon grass plant CT-2, which is in the top of the photograph with the zymogram pattern, of the closest known variety C84-135 in the bottom of the photograph, both grasses were taken from the same test area.

Figure 5:
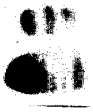

FIG. 5 this photograph shows the electrophoresis zymogram patterns of the phosphoglucomutase (GPM) isoenzyme banding pattern, of the new claimed variety of Cynodon Dactylon grass plant CT-2, which is the top of the photograph with the zymogram pattern of the closest known variety of Cynodon Dactylon grass plant C84-135, in the bottom of the photograph, both grasses were taken from the same test area.

A detailed description of the new and distinct variety of Cynodon Dactylon grass plant CT-2 is:

(a) An attractive very dark green color, color number 147 v.d.G of the ISCC-NBS centroid color chart.

(b) The grass is low-growing, erect in habit.

(c) The grass spreads by stolons and rhizomes, forming a dense, uniform surface, with an extensive root system; the stolon internodal spacings 2–3 centimeters apart.

(d) Culms vary in height from 12–16 centimeters, (e) Leaves folded in bud shoot.

(f) The leaf blade is flat, and gradually tapering to an acute point.

(g) The first mature leaf is 3–4 millimeters in width and 60–90 millimeters in length.

(h) The grass blade is pubescent, on the mature upper and lower leaf surface.

(i) The ligule is a ring of hairs.

(j) Auricles are absent.

(k) The collar is continuous narrow band.

(l) The sheath is pubescent, split with margins overlapping.

(m) The entire plant is pubescent.

(n) The internodal spaces on the stolons are 2–3 centimeters and on the culms 2.5–3.5 centimeters.

(o) The inflorescence consists of 3–4 spikes at the top of the main stem, deflexed at maturity from 35–40 millimeters long.

(p) The spiklets are glabrous in two rows 2–3 millimeters long, blunt at their base pointed at their tips, borne singly on short branches and glumes are present; the spiklet contains stigmas of very deep purplish red color, color number 257 v.deep pr of the ISCC-NBS centroid color chart with newly formed anthers of light yellow green color, color number 119.lYG of the ISCC-NBS centroid color chart.

A detailed description of the closest known variety of Cynodon Dactylon grass plant is:

(a) An attractive, dark olive green color, color number 126.d.OL G of the ISCC-NBS centroid color chart.

(b) The grass is low-growing, erect in habit.

(c) The grass spreads by stolons and rhizomes, forming a dense uniform surface with an extensive root system.

(d) Culms vary in height from 10–14 centimeters.

(e) Leaves folded in but shoot.

(f) The blade is V-shaped in cross-section, keeled and gradually tapering to an acute point.

(g) The first mature leaf is 2–3 millimeters in width and 50–70 millimeters in length.

(h) The grass blade is pubescent on the mature upper leaf surface with a few hairs tufted at the sides of the ligule.

(i) The ligule is a fringe of hairs.

(j) Auricles are absent.

(k) The collar is continuous narrow band.

(l) The sheath is glabrous, split with margins overlapping.

(m) The entire plant is glabrous except for a few hairs tufted at the sides of the ligule and pubescent on the mature upper leaf surface.

(n) The internodal spaces on the stolons are 1.5–2 centimeters and on the culms 2–3 centimeters, the width of the stolon thickness is 1–1.5 millimeters.

(o) The inflorescence consists of 3–4 spikes at the top of the main stem, deflexed at maturity from 30–35 millimeters long.

(p) The spiklets are glabrous in two rows 2–3 millimeters long, blunt at their base pointed at their tips, borne singly on short branches and glumes are present; the spiklet contains stigmas of very dark purplish red color, color number 260 v.d.pr of the ISCC-NBS centroid color chart with newly formed anthers of grayish red color, color number 19 GY.red of the ISCC-NBS centroid color chart.

REFERENCE

1. Lin Wu, H. Harivandi, James A. Harding and William B. Davis. 1984. Identification of Kentucky Bluegrass Cultivars with Esterase and Phosphoglucomutase Isoenzyme Markers, Crop Science. Vol. 24 July–August 1984, P. 763–768.

Having now described the new and distinct variety of Cynodon Dactylon grass plant, which I have developed, discovered and asexually reproduced, I claim:

1. A new and distinct variety of Cynodon Dactylon grass plant herein described and illustrated, a new variety that I developed, discovered and asexually repropagated; this new variety of Cynodon Dactylon grass plant having a very dark green leaf blade color, with newly formed anthers before dehiscence of light yellow green color, with stolon and culm internodal spaces farther apart, than the closest known variety of Cynodon Dactylon grass plant C84-135; this new claimed variety CT-2 being entirely pubescent and producing a significant lack of thatch build-up, when compared to the closest known variety C84-135; this new claimed variety of Cynodon Dactylon grass plant CT-2, showing distinct uniqueness with the electrophoresis isoenzyme banding patterns herein shown, when compared to the closest known variety of Cynodon Dactylon grass plant C84-135.

* * * * *

HUBERT F.WHITING
SHEET 2 OF 2